(12) United States Patent
Ragab et al.

(10) Patent No.: US 8,828,018 B2
(45) Date of Patent: Sep. 9, 2014

(54) BONE CAGE PLACEMENT DEVICE

(76) Inventors: Ashraf A. Ragab, Largo, FL (US); James A. Rinner, Franksville, WI (US)

(*) Notice: Subject to any disclaimer, the term of this patent is extended or adjusted under 35 U.S.C. 154(b) by 173 days.

(21) Appl. No.: 12/966,361

(22) Filed: Dec. 13, 2010

(65) Prior Publication Data
US 2012/0150241 A1 Jun. 14, 2012

(51) Int. Cl.
*A61B 17/58* (2006.01)
*A61F 2/28* (2006.01)
*A61F 2/30* (2006.01)
*A61F 2/44* (2006.01)
*A61F 2/46* (2006.01)

(52) U.S. Cl.
CPC ........ *A61F 2/4611* (2013.01); *A61F 2002/2835* (2013.01); *A61F 2002/30594* (2013.01); *A61F 2002/30904* (2013.01); *A61F 2002/4475* (2013.01); *A61F 2002/30492* (2013.01); *A61F 2002/30451* (2013.01); *A61F 2002/4628* (2013.01); *A61F 2002/30579* (2013.01); *A61F 2/447* (2013.01); *A61F 2002/30472* (2013.01); *A61F 2002/4623* (2013.01); *A61F 2002/30629* (2013.01)
USPC .......................................................... 606/99

(58) Field of Classification Search
CPC .................................................. A61F 2/4611
USPC ............................... 606/99; 623/17.11–17.16
See application file for complete search history.

(56) References Cited

U.S. PATENT DOCUMENTS

| | | | |
|---|---|---|---|
| 6,080,155 A | 6/2000 | Michelson | |
| 6,083,225 A | 7/2000 | Winslow et al. | |
| 6,174,311 B1 | 1/2001 | Branch et al. | |
| 6,610,065 B1 | 8/2003 | Branch et al. | |
| 6,666,866 B2 | 12/2003 | Martz et al. | |
| 6,984,245 B2 | 1/2006 | McGahan et al. | |
| 7,081,122 B1 | 7/2006 | Reiley et al. | |
| 7,235,082 B2 | 6/2007 | Bartish et al. | |
| 7,244,258 B2 | 7/2007 | Burkus et al. | |
| 7,247,169 B1 | 7/2007 | Lo et al. | |
| D608,001 S | 1/2010 | Reardon | |
| 7,655,027 B2 | 2/2010 | Michelson | |
| 7,776,049 B1 | 8/2010 | Curran et al. | |
| D626,227 S | 10/2010 | Leroy et al. | |
| 7,811,287 B2 | 10/2010 | Errico et al. | |
| 2006/0004376 A1* | 1/2006 | Shipp et al. | 606/99 |
| 2006/0030856 A1* | 2/2006 | Drewry et al. | 606/90 |
| 2008/0306488 A1* | 12/2008 | Altarac et al. | 606/99 |

* cited by examiner

*Primary Examiner* — Nicholas Woodall
(74) *Attorney, Agent, or Firm* — Absolute Technology Law Group, LLC

(57) ABSTRACT

A bone cage placement device used to insert and position a bone cage in the disc space. Once the bone cage is positioned, a selector tool is inserted into the center aperture of the bone cage placement device. The end of the selector tool has a cam lift driving feature which is used to rotate the cam lift of the bone cage and expand the bone cage to the desired height. The selector tool is removed, and a graft placement tool and plunger are used to insert bone graft material into the plug. An end plug installation tool and installer are then used to insert an end plug to prevent leakage of material from the bone cage. The bone cage is released from the bone cage placement device, which is then removed from the patient's body.

20 Claims, 17 Drawing Sheets

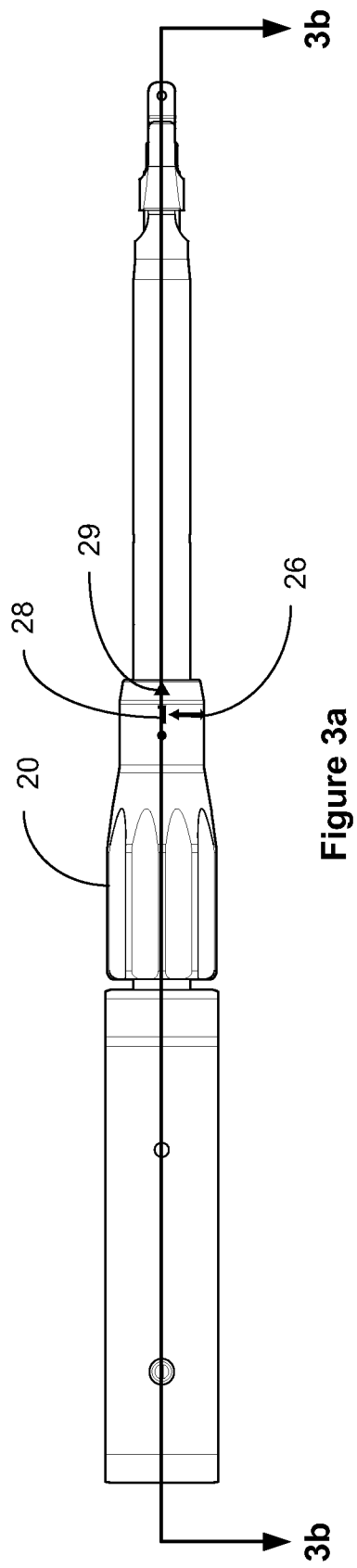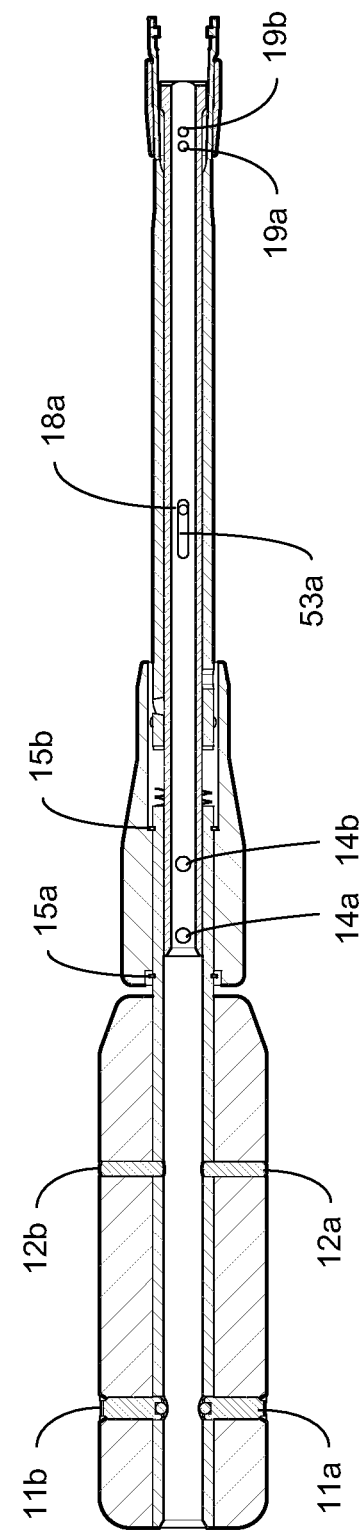
Figure 3a
Figure 3b

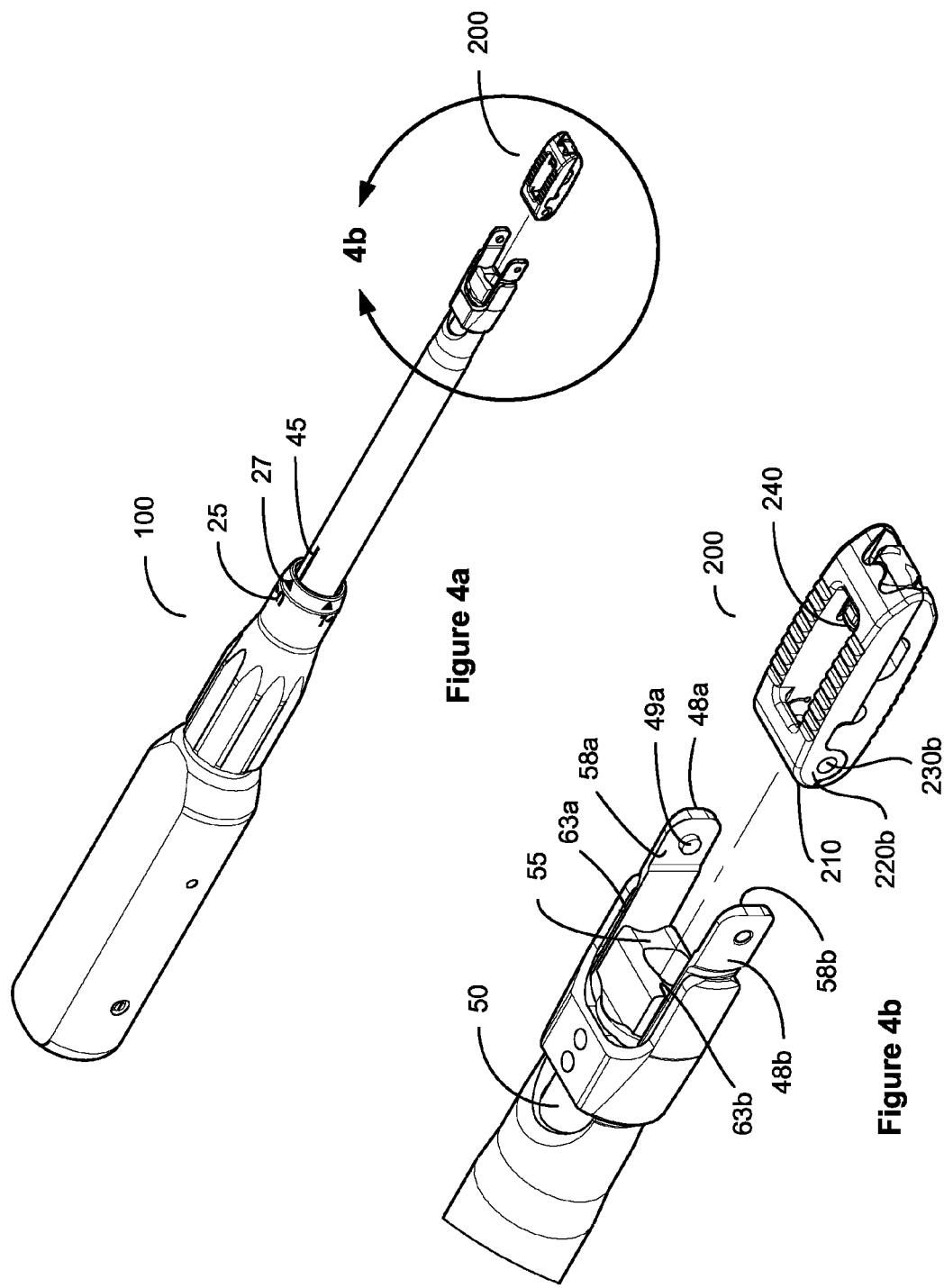

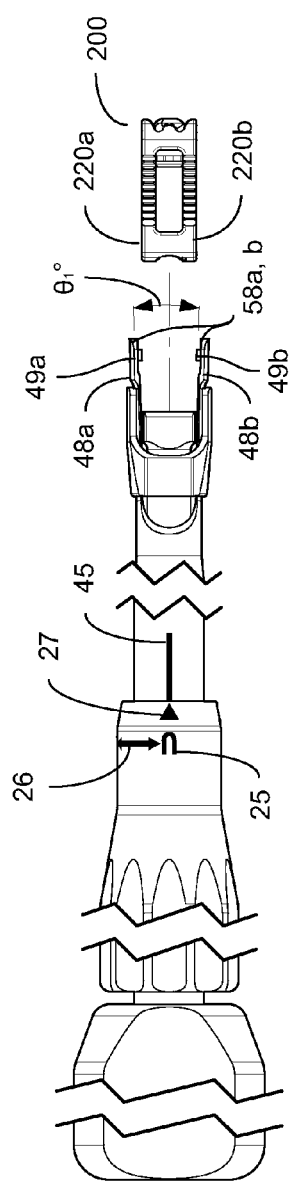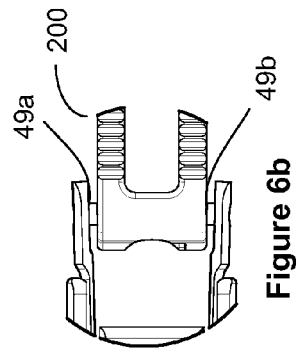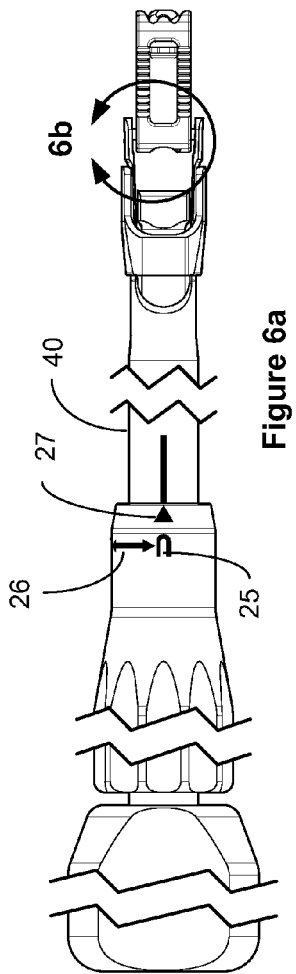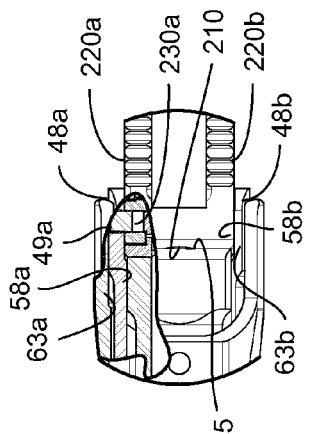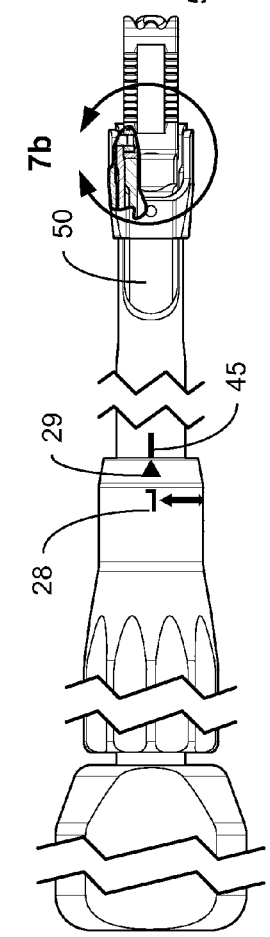
Figure 5
Figure 6a
Figure 6b
Figure 7a
Figure 7b

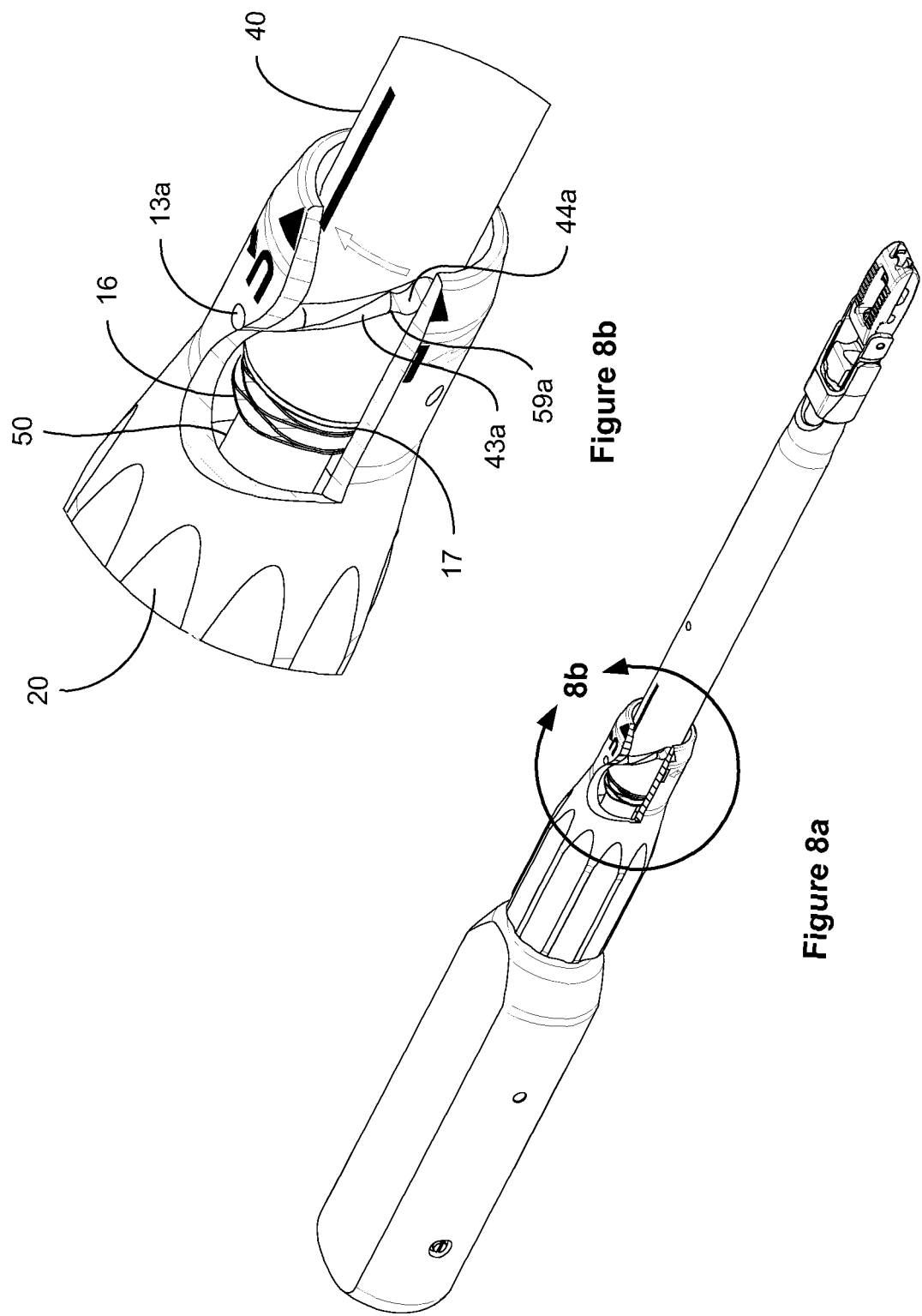

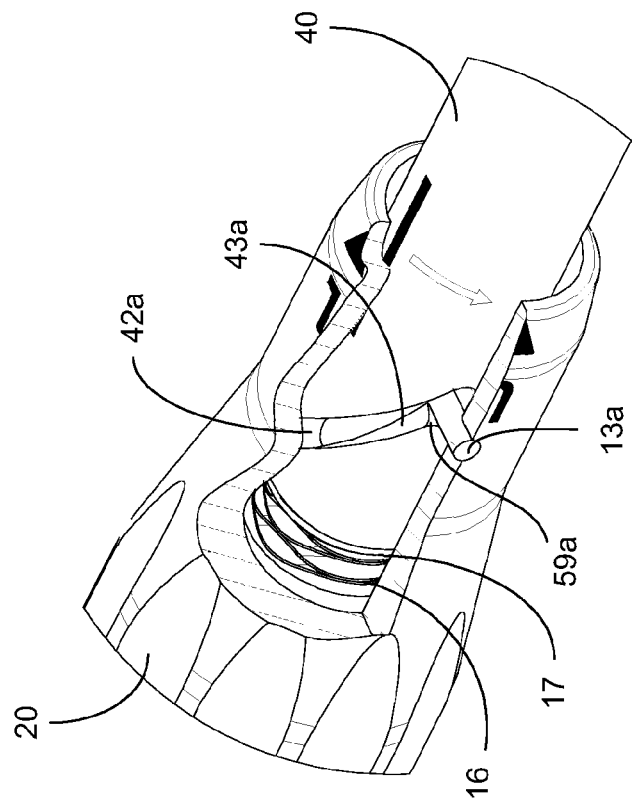
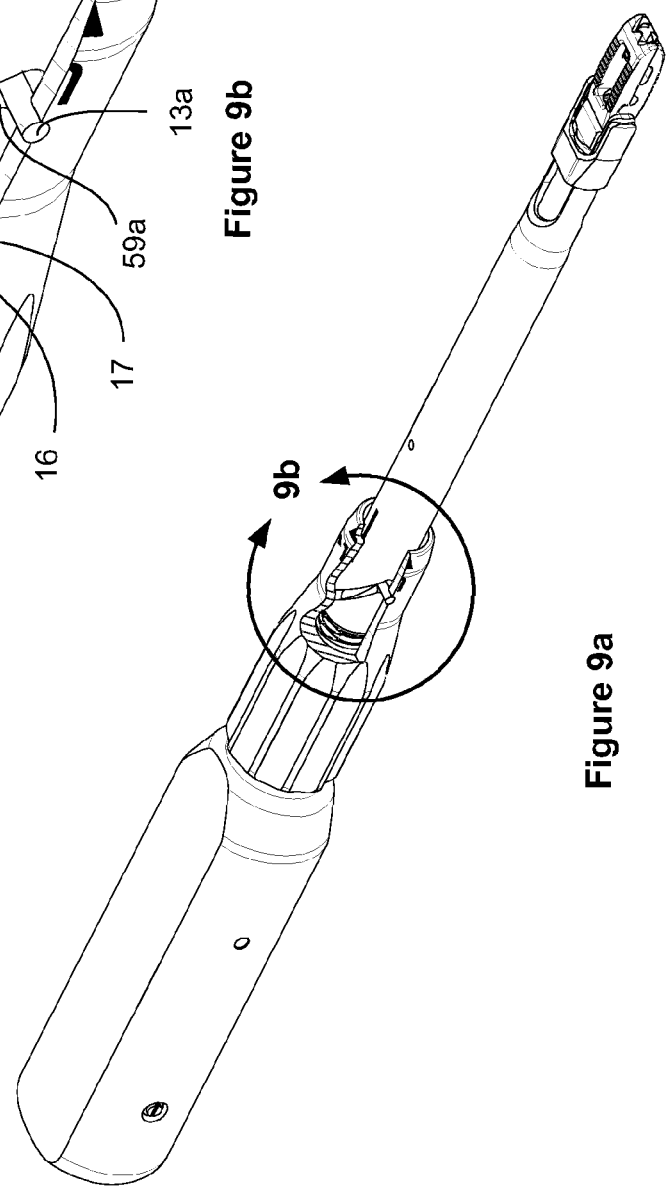
Figure 9b
Figure 9a

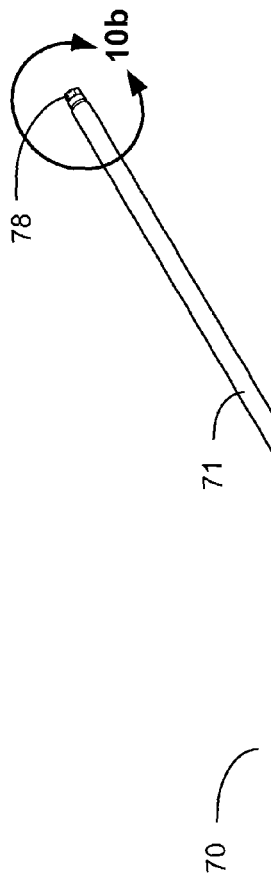
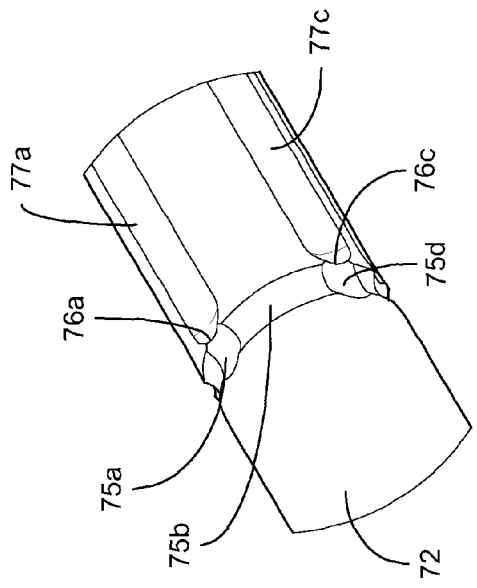
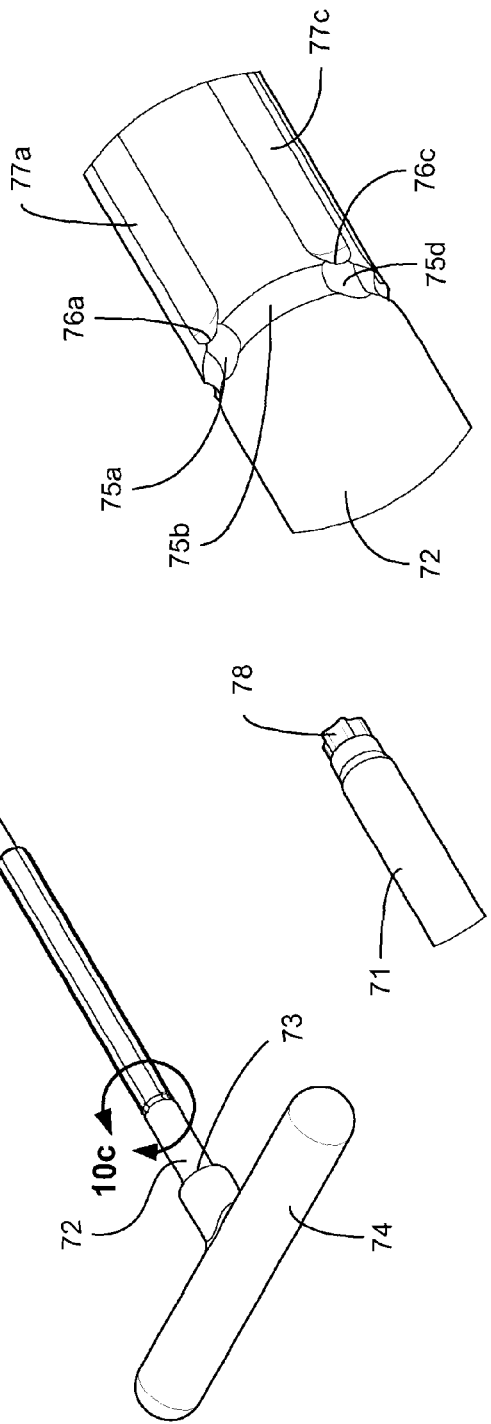

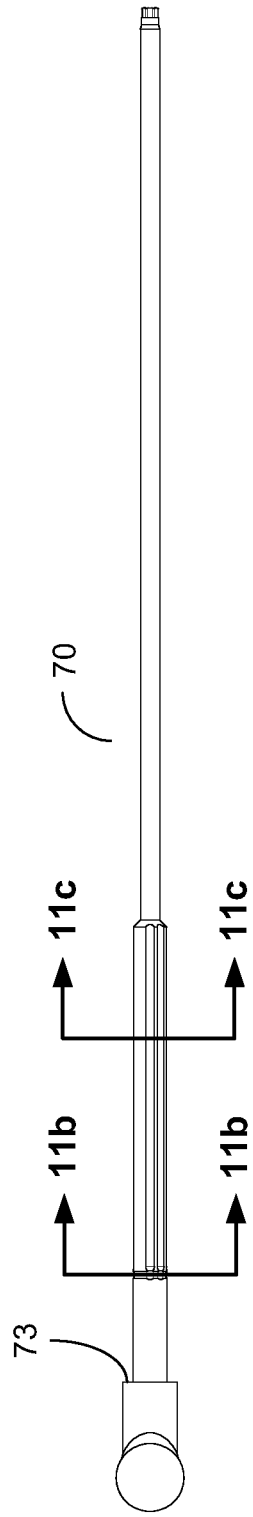
Figure 11a
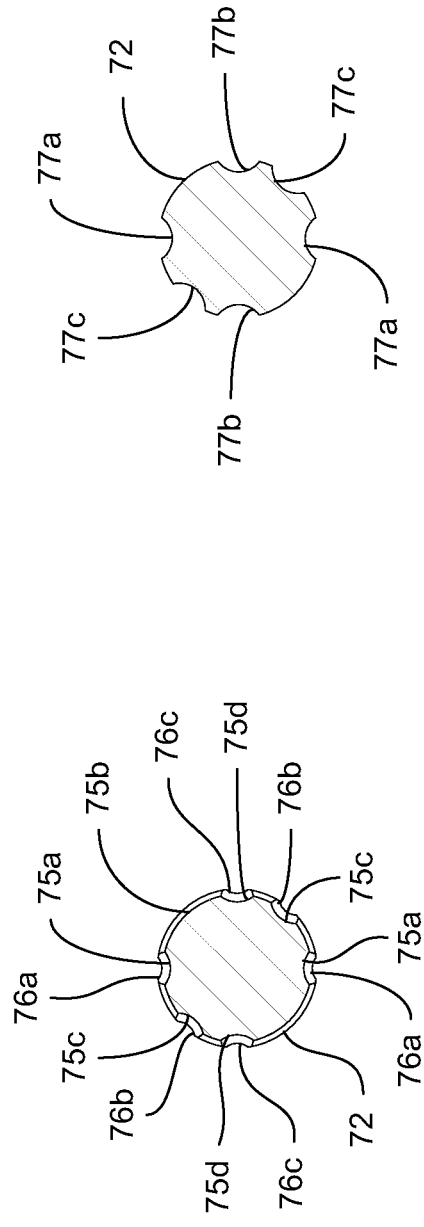
Figure 11b
Figure 11c

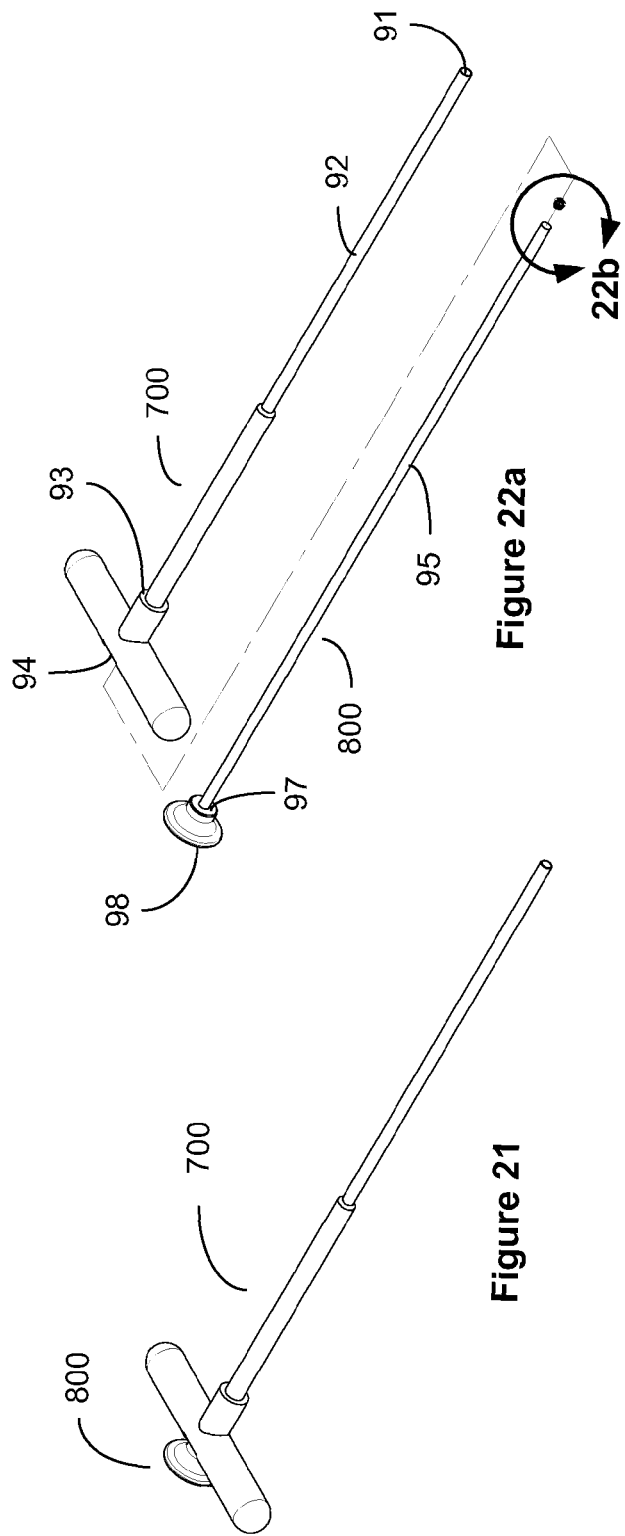
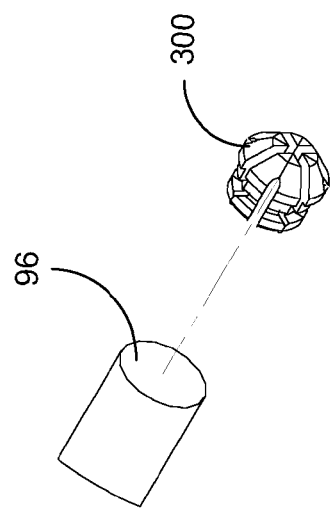
Figure 22a
Figure 22b
Figure 21

BONE CAGE PLACEMENT DEVICE

FIELD OF INVENTION

The present invention relates to the field of implants and more particularly to a device for inserting, adjusting, and expanding an expandable and adjustable bone cage with a rotatable cam lift.

BRIEF DESCRIPTION OF THE DRAWINGS

FIG. 2b illustrates a cross sectional view of an exemplary embodiment of a bone cage placement device in the unloaded position taken along line 2b of FIG. 2a.

FIG. 3a illustrates a right side view of an exemplary embodiment of a bone cage placement device in the unloaded position.

FIG. 3b illustrates a cross sectional view of an exemplary embodiment of a bone cage placement device in the unloaded position taken along line 3b of FIG. 3a.

FIG. 4a illustrates an isometric view of an exemplary embodiment of a bone cage placement device and an expandable bone cage.

FIG. 4b illustrates a close-up isometric view of area 4b of FIG. 4a.

FIG. 5 illustrates a top view of an exemplary embodiment of a bone cage placement device in the unloaded position with an expandable bone cage in the unloaded position.

FIG. 6a illustrates a top view of an exemplary embodiment of a bone cage placement device in the unloaded position with an expandable bone cage in the loading position.

FIG. 6b illustrates an enlarged view of area 6b of FIG. 6a.

FIG. 7a illustrates a top view of an exemplary embodiment of a bone cage placement device in the loaded position with an expandable bone cage in the loaded position.

FIG. 7b illustrates an enlarged view of area 7b of FIG. 7a.

FIG. 8a illustrates an isometric view of an exemplary embodiment of a bone cage placement device in the unloaded position within an expandable bone cage in the loading position.

FIG. 8b illustrates an enlarged view of area 8b of FIG. 8a.

FIG. 9a illustrates an isometric view of an exemplary embodiment of a bone cage placement device in the loaded position with an expandable bone cage in the loaded position.

FIG. 9b illustrates an enlarged view of area 9b of FIG. 9a.

FIG. 10a illustrates an isometric view of an exemplary embodiment of a selector tool for a bone cage placement device.

FIG. 10b illustrates an enlarged view of area 10b of FIG. 10a.

FIG. 10c illustrates an enlarged view of area 10c of FIG. 10a.

FIG. 11a illustrates a side view of an exemplary embodiment of a selector tool for a bone cage placement device.

FIG. 11b illustrates a cross sectional view taken along line 11b of FIG. 11a.

FIG. 11c illustrates a cross sectional view taken along line 11c of FIG. 11a.

FIG. 12b illustrates an enlarged view of area 12b of FIG. 12a.

FIG. 13b illustrates an enlarged view of area 13b of FIG. 13a.

FIG. 14b illustrates an enlarged view of area 14b of FIG. 14a.

FIG. 15b illustrates a cross sectional view taken along line 15b of FIG. 15a.

FIG. 15c illustrates a cross sectional view taken along line 15c of FIG. 15a.

FIG. 19b illustrates a cross sectional view taken along line 19b of FIG. 19a.

FIG. 20b illustrates a cross sectional view taken along line 20b of FIG. 20a.

FIG. 21 illustrates an isometric view of an exemplary embodiment of an end plug installation tool and an end plug installer for a bone cage placement device.

FIG. 22a illustrates an exploded isometric view of an exemplary embodiment of an end plug installation tool, an end plug installer, and an end plug.

FIG. 22b illustrates an enlarged view of area 22b of FIG. 22a.

FIG. 23b illustrates a cross sectional view taken along line 23b of FIG. 23a.

FIG. 24b illustrates a cross sectional view taken along line 24b of FIG. 24a.

GLOSSARY

Figure 1:
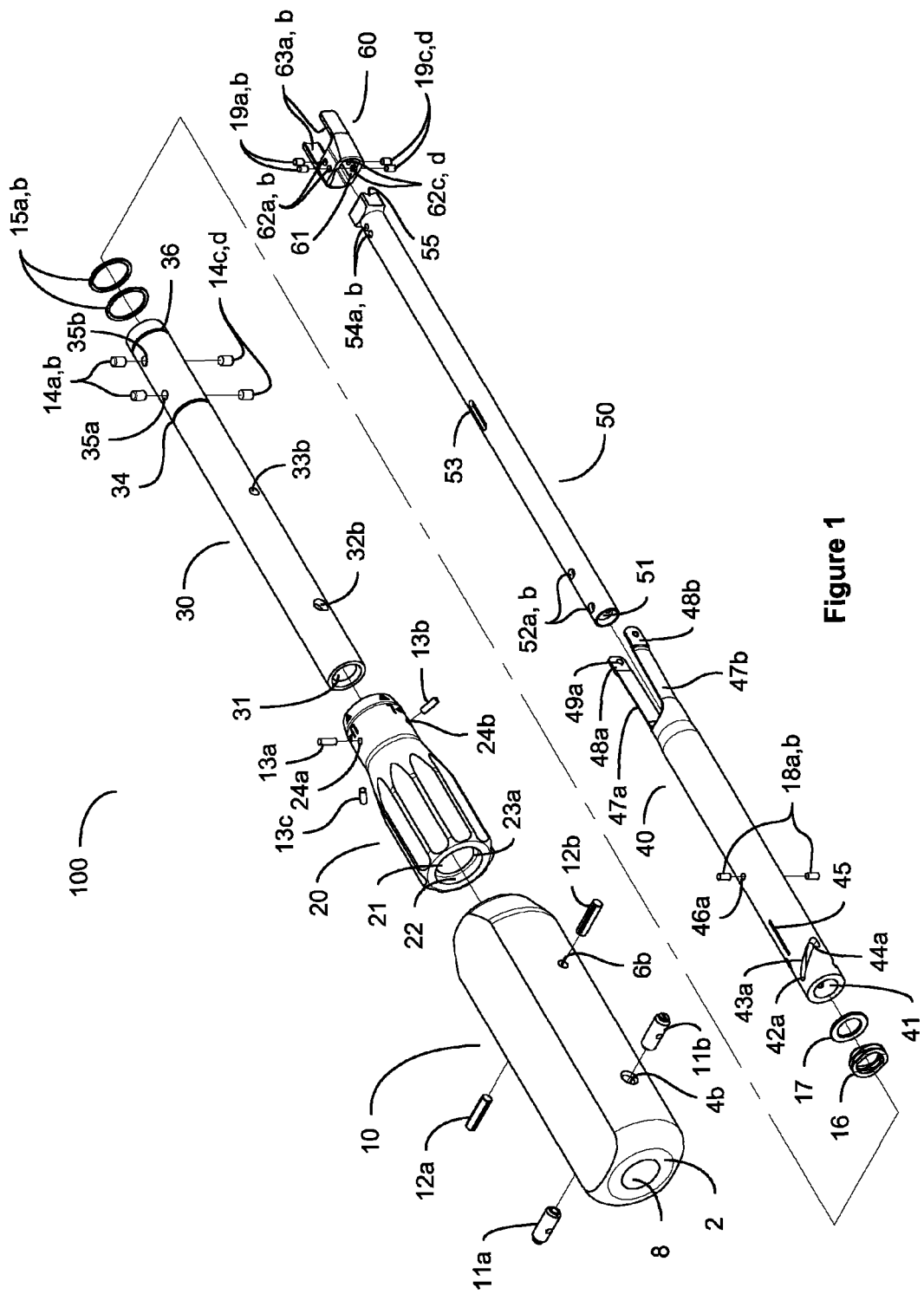
FIG. 1 illustrates an exploded view of an exemplary embodiment of a bone cage placement device.

As used herein, the term "bone cage" refers to an implant that is inserted into the space between vertebrae bodies replacing a damaged vertebra disc and restoring the spacing between the vertebrae.

As used herein, the term "bone graft material" refers to the substance placed in a bone cage that facilitates the growth of new bone tissue. Bone graft material may be artificial (e.g., created from ceramics), synthetic (e.g., made from hydroxylapatite or calcium carbonate), or a natural substance (e.g., bone harvested from another bone in the patient's body (autograft), bone taken from a donor (allograft), or bone morphogenetic proteins (BMPs).

As used herein, the term "cam lift" refers to a component with a rotational driving surface used to expand a bone cage. A cam lift may further serve a safety and control function. For example, a cam lift may be structurally designed to allow only a certain amount of expansion (e.g., 1 mm to 2 mm) to prevent over rotation.

As used herein, the term "cam lift driving feature" refers to the portion of a selector tool used to rotate a cam lift of an expandable bone cage.

As used herein, the term "end plug" refers to a component that prevents leakage of bone graft material from a bone cage.

As used herein, the term "selector tool" refers to an instrument used to expand an expandable bone cage.

BACKGROUND

Spinal fusion surgery for degenerative disc disease involves removing the damaged disc and replacing it with bone grafted from another site on the patient's body, bone from a donor, or artificial or synthetic bone graft material that stimulates bone growth to fuse, or join, the two vertebrae together to stabilize the spine. In all spinal interbody fusion surgeries, disc material is removed. A spacer, referred to as a "cage" is then inserted into the disc space.

Bone cages require the use of specialized instruments for insertion and adjustment. Many bone cages require the use of multiple instruments in order to properly insert and adjust the bone cage. This is not desirable because the removal and insertion of additional instruments during spinal fusion surgery can cause damage to the surrounding nerves as well as the spinal cord.

There are many types of bone cages known in the art. One example of an expandable bone cage is disclosed by U.S. patent application Ser. No. 12/848,797, filed on Aug. 2, 2010, and herein incorporated by reference. U.S. patent application Ser. No. 12/848,797 discloses a bone cage with components that allow for controlled expansion.

Other bone cages known in the art are filled with bone graft material outside of the body before the cage is inserted into the disc space. When the cage is hammered during insertion, bone graft material may leak from the bone cage and into the spinal canal where it can damage the nerves.

It is desirable to have a bone cage placement device that allows bone graft material to be inserted into the bone cage after it has been inserted into the disc space.

It is desirable to have a bone cage placement device that allows a bone cage to be inserted, adjusted, and expanded, and which allows bone graft material to be inserted and an end plug positioned using a single device.

SUMMARY OF THE INVENTION

The present invention is a bone cage placement device and system for inserting and expanding the expandable bone cage disclosed in U.S. patent application Ser. No. 12/848,797, filed on Aug. 2, 2010, and herein incorporated by reference.

The bone cage placement device comprised of a handle, a selector knob, a handle shaft, a sliding implant engaging component, an abutment shaft, and a reduction yoke and is used to insert and position a bone cage in the disc space. Once the bone cage is positioned, a selector tool is inserted into the center aperture of the bone cage placement device. The end of the selector tool has a cam lift driving feature which is used to rotate the cam lift of the bone cage and expand the bone cage to the desired height. The selector tool is removed, and a graft placement tool and plunger are used to insert bone graft material into the plug. An end plug installation tool and installer are then used to insert an end plug to prevent leakage of material from the bone cage.

During the spinal fusion procedure, the bone cage placement device stays attached to the implants while the additional instruments are sild down the center aperture of the instrument, thus providing protection to the delicate spinal cord and nerve roots.

DETAILED DESCRIPTION OF INVENTION

For the purpose of promoting an understanding of the present invention, references are made in the text to exemplary embodiments of a bone cage placement device, only some of which are described herein. It should be understood that no limitations on the scope of the invention are intended by describing these exemplary embodiments. One of ordinary skill in the art will readily appreciate that alternate but functionally equivalent components, placement, and designs may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1 illustrates an exploded view of an exemplary embodiment of bone cage placement device 100 comprised of handle 10, selector knob 20, handle shaft 30, sliding implant engaging component 40, implant abutment shaft 50, and reduction yoke 60.

Bone cage placement device 100 is assembled by pinching flexible arms 47a, 47b of sliding implant engaging component 40 together and sliding reduction yoke 60 over flexible arms 47a, 47b until radial outer surfaces 48a, 48b of sliding implant engaging component 40 protrude past radial inner surfaces 63a, 63b of reduction yoke 60. When flexible arms 47a, 47b are released, flexible arms 47a, 47b rest against radial inner surfaces 63a, 63b of reduction yoke 60 (see FIG. 4b).

When sliding implant engaging component 40 and reduction yoke 60 are assembled, the end of implant abutment shaft 50 opposite concave abutment surface 55 is inserted between flexible arms 47a, 47b and into implant abutment shaft aperture 41 of implant abutment shaft 50 so that the end of implant abutment shaft 50 protrudes from sliding implant engaging component 40. Implant abutment shaft 50 is secured inside sliding implant engaging component 40 by inserting alignment pins 18a, 18b through apertures 46a, 46b (46b not visible) in the top and bottom of sliding implant engaging component 40 and into alignment slots 53a, 53b (53b not visible) in the top and bottom of implant abutment shaft 50.

Reduction yoke 60 is then secured to implant abutment shaft 50 by inserting dowel pins 19a, 19b, 19c, 19d through apertures 62a, 62b, 62c, 62d in the top and bottom of reduction yoke 60 and into apertures 54a, 54b, 54c, 54d (54c, 54d not visible) in the top and bottom of implant abutment shaft 50. Alignment pins 18a, 18b and dowel pins 19a, 19b, 19c, 19d are welded in place and the welds are polished until even with the outer surface of sliding implant engaging component 40 and reduction yoke 60, respectively.

Figure 2A:
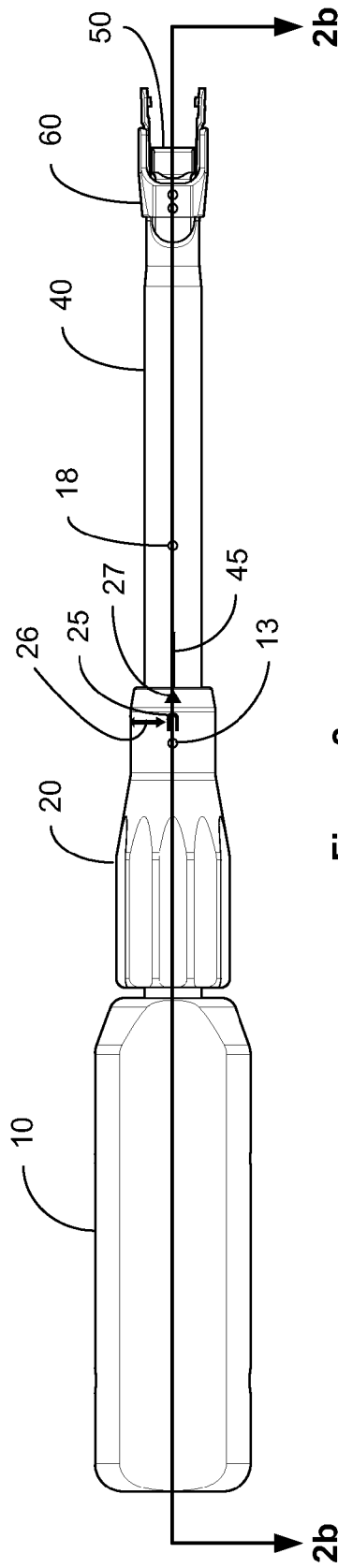
FIG. 2a illustrates a top view of an exemplary embodiment of a bone cage placement device in the unloaded position.
Figure 2B:
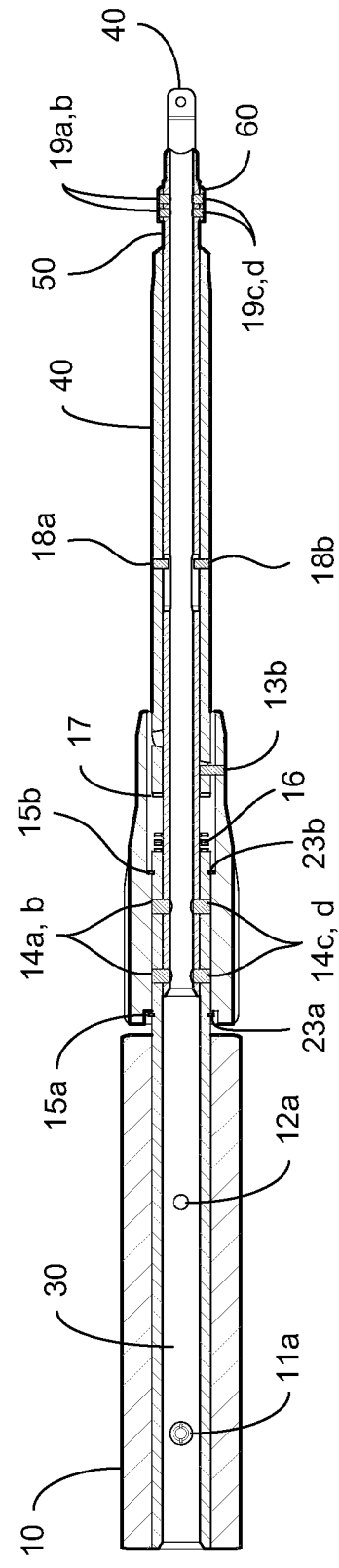

Positional spring thrust washer 17 and positional spring 16 are inserted onto the end of implant abutment shaft 50 that protrudes from sliding implant engaging component 40 (see FIGS. 2b and 3b). When bone cage placement device 100 is in the unloaded position, positional spring thrust washer 17 and positional spring 16 are free to float on implant abutment shaft 50.

Handle shaft 30 is inserted over the end of implant abutment shaft 50 and secured to implant abutment shaft 50 by inserting dowel pins 14a, 14b, 14c, 14d through apertures 35a, 35b, 35c, 35d (35c, 35d not visible) in handle shaft 30 and into apertures 52a, 52b, 52c, 52d (52c, 52d not visible) in implant abutment shaft 50. Dowel pins 14a, 14b, 14c, 14d are welded in place and the welds polished until even with handle shaft 30.

Retaining ring 15b is slid over handle shaft 30 and into distal groove 36 on handle shaft 30. Selector knob 20 is then slid onto handle shaft 30 and onto sliding implant engaging component 40. Selector knob 20 is positioned so that shoulder 23b abuts retaining ring 15b (see FIG. 2b) and U-shaped position mark 25 on selector knob 20 is aligned with positional mark 45 on sliding implant engaging component 40 (see FIG. 2a).

To secure selector knob 20 to sliding implant engaging component 40, cam follower pins 13a, 13b, 13c are inserted through apertures 24a, 24b, 24c (24c not visible) in selector knob 20 and into cam slots 43a, 43b, 43c (43b, 43c not visible) in sliding implant engaging component 40. When bone cage placement device 100 is in the unloaded position, cam follower pins 13a, 13b, 13c are in unloaded positions 42a, 42b, 42c (42b, 42c not visible) of cam slots 43a, 43b, 43c and when bone cage placement device 100 is in the loaded position, cam follower pins 13a, 13b, 13c are in loaded positions 44a, 44b, 44c (44b, 44c not visible) of cam slots 43a, 43b, 43c. Cam follower pins 13a, 13b, 13c are welded in place and the welds polished until even with selector knob 20.

When selector knob 20 is in place, retaining ring 15a is inserted over the end of handle shaft 30 into proximal groove 34 so that it abuts shoulder 23a of selector knob 20. Selector knob 20 further includes retaining ring groove 22 which helps to secure retaining ring 15a.

Handle 10 is then slid onto handle shaft 30 and secured by inserting dowel pins 12a, 12b through apertures 6a, 6b (6a not visible) on each side of handle 10 and into apertures 33a, 33b (33a not visible) in handle shaft 30. In addition, ball spring plungers 11a, 11b are inserted through apertures 4a, 4b (4a not visible) on each side of handle 10 and into apertures 32a, 32b (32a not visible) in handle shaft 30.

FIG. 2a illustrates a top view of an exemplary embodiment of assembled bone cage placement device 100 in the unloaded position. Selector knob 20 includes position marks 25, 26, 27, 28 (FIG. 3a), and 29 (FIG. 3a), which designate whether bone cage placement device 100 is in the unloaded or loaded position. Each position mark appears twice on selector knob 20, equidistance apart.

In the embodiment shown, position mark 25 is a "U" for the unloaded position, position mark 26 is a radial arrow, and position marks 27, 29 (see FIG. 3a) are triangular arrows. When bone cage placement device 100 is in the unloaded position, U-shaped position mark 25 and triangular arrow position mark 27 align with positional mark 45 on sliding implant engaging component 40. Radial arrow position mark 26 designates in which direction selector knob 20 may be turned.

Selector knob 20 controls sliding implant engaging component 40 and is rotated to grasp and release expandable bone cage 200. Cam follower pins 13a, 13b, and 13c (see FIG. 1) are equally spaced around selector knob 20. Cam follower pins 13a, 13b, and 13c allow for smooth turning and operation of selector knob 20.

FIG. 2b illustrates a cross sectional view of an exemplary embodiment of bone cage placement device 100 in the unloaded position taken along line 2b of FIG. 2a. In the embodiment shown, bone cage placement device 100 is in the unloaded position. When bone cage placement device 100 is in the unloaded position, positional spring 16 and positional spring thrust washer 17 float freely on sliding implant engagement component 40.

Visible are dowel pins 14a, 14b, 14c, 14d which secure implant abutment shaft 50 inside handle shaft 30, dowel pins 19a, 19b, 19c, 19d which secure reduction yoke 60 to implant abutment shaft 50, and alignment pins 18a, 18b which align sliding implant engaging component 40 and implant abutment shaft 50. Alignment pins 18a, 18b move in alignment slots 53a, 53b (not visible, See FIG. 3b) allowing for longitudinal movement while preventing rotation of sliding implant engaging component 40.

Also visible are retaining rings 15a, 15b which abut shoulders 23a, 23b. Shoulders 23a, 23b allow for free radial movement of selector knob 20, but limit the longitudinal movement of selector knob 20 helping to secure selector knob 20 in position.

FIG. 3a illustrates a right side view of an exemplary embodiment of an assembled bone cage placement device 100 in the unloaded position. Visible are L-shaped position mark 28, triangular arrow position mark 29, and radial arrow position mark 26 on selector knob 20.

FIG. 3b illustrates a cross sectional view of an exemplary embodiment of bone cage placement device 100 in the unloaded position taken along line 3b of FIG. 3a. Visible are ball spring plungers 11a and 11b, dowel pins 12a and 12b, dowel pins 14a, 14b, alignment pin 18a, alignment slot 53a, dowel pins 19a and 19b and retaining rings 15a, 15b.

FIG. 4a illustrates an isometric view of an exemplary embodiment of bone cage placement device 100 and expandable bone cage 200. In the embodiment shown, bone cage placement device 100 is in the unloaded position and U-shaped position mark 25 and triangular arrow position mark 27 are aligned with position mark 45 on sliding implant engaging component 40.

FIG. 4b illustrates a close-up isometric view of area 4b of FIG. 4a. Implant abutment shaft 50 has concave abutment surface 55 which mates against convex mating surface 210 of expandable bone cage 200. The end of sliding implant engaging component 40 has radial outer surfaces 48a, 48b and flat inner surfaces 58a, 58b. Each of flat inner surfaces 58a, 58b has pin 49a, 49b (49b not visible).

Visible are radial inner surfaces 63a, 63b of reduction yoke 60. When bone cage placement device 100 is in the unloaded position, radial inner surfaces 63a, 63b of reduction yoke 60 are not in contact with radial outer surfaces 48a, 48b of sliding implant engaging component 40.

Also visible on expandable bone cage 200 are flat surfaces 220a, 220b (220a not visible), holes 230a, 230b (230a not visible), and cam lift 240. When expandable bone cage 200 is in the loading or loaded position, pins 49a, 49b engage holes 230a, 230b of expandable bone cage 200 (See FIGS. 6b and 7b).

FIG. 5 illustrates a top view of an exemplary embodiment of bone cage placement device 100 in the unloaded position with expandable bone cage 200 in the unloaded position. Selector knob 20 is rotated so that U-shaped position mark 25 and triangular arrow position mark 27 align with positional mark 45 on sliding implant engaging component 40.

Visible are radial outer surfaces 48a, 48b, flat inner surfaces 58a, 58b, and pins 49a, 49b on sliding implant engaging component 40 and flat surfaces 220a and 220b on expandable bone cage 200. When bone cage placement device 100 is in the unloaded position, flat inner surfaces 58a, 58b of sliding implant engaging component 40 are angled slightly outward ($\theta_1°$).

FIG. 6a illustrates a top view of an exemplary embodiment of bone cage placement device 100 in the unloaded position with expandable bone cage 200 in the loading position. When expandable bone cage 200 is in the loading position, bone cage placement device 100 is still in the unloaded position and selector knob 20 is rotated so that U-shaped position mark 25 and triangular arrow position mark 27 align with position mark 45 on sliding implant engaging component 40.

FIG. 6b illustrates an enlarged view of area 6b of FIG. 6a. When expandable bone cage 200 is in the loading position, pins 49a, 49b of sliding implant engaging component 40 engage holes 230a, 230b (not visible, see FIG. 4b) of expandable bone cage 200.

FIG. 7a illustrates a top view of an exemplary embodiment of bone cage placement device 100 in the loaded position with expandable bone cage 200 in the loaded position. When bone cage placement device 100 is in the loaded position, selector knob 20 is rotated so that L-shaped position mark 28 and triangular arrow position mark 29 align with position mark 45 on sliding implant engaging component 40. When bone cage placement device 100 is in the loaded position, position mark 45 appears shorter than when bone cage placement device 100 is in the unloaded position because sliding implant engaging component 40 slides in the proximal direction when selector knob 20 is rotated in a clockwise direction from an unloaded to a loaded position.

FIG. 7b illustrates an enlarged view of area 7b of FIG. 7a. When selector knob 20 is rotated clockwise, radial outer surfaces 48a, 48b of sliding implant engaging component 40 come in contact with radial inner surfaces 63a, 63b of reduction yoke 60 and cause flat inner surfaces 58a, 58b to become parallel. When flat inner surfaces 58a, 58b are parallel, flat inner surfaces 58a, 58b are in contact with flat surfaces 220a, 220b of expandable bone cage 200 and pins 49a, 49b enter into holes 230a, 230b (230b not visible) of expandable bone cage 200 to retain expandable bone cage 200 in bone cage placement device 100. In addition, when expandable bone cage 200 is in the loaded position, convex mating surface 210 of expandable bone cage 200 mates against concave abutment surface 55 of implant abutment shaft 50.

FIG. 8a illustrates an isometric view of an exemplary embodiment of bone cage placement device 100 in the unloaded position with expandable bone cage 200 in the loading position.

FIG. 8b illustrates an enlarged view of area 8b of FIG. 8a. When bone cage placement device 100 is in the unloaded position with expandable bone cage 200 in the loading position, cam follower pins 13a, 13b, 13c (13b, 13c not visible) are in cam slots 43a, 43b, 43c (43b, 43c not visible) and are resting against the hidden proximal end of cam slots 42a, 42b, 42c (not visible). When selector knob 20 is rotated counterclockwise (see arrow), cam follower pins 13a, 13b, 13c travel over cam-over surfaces 59a, 59b, 59c (59b, 59c not visible) and along cam slots 43a, 43b, 43c, causing sliding implant engaging component 40 to slide longitudinally in the proximal direction until cam follower pins 13a, 13b, 13c rest in their final unloaded positions in cam slots 42a, 42b, 43c.

Also visible are positional spring 16 and positional spring thrust washer 17. When bone cage placement device 100 is in the unloaded position, positional spring 16 and spring thrust washer 17 are loosely positioned around implant abutment shaft 50.

FIG. 9a illustrates an isometric view of an exemplary embodiment of bone cage placement device 100 in the loaded position with expandable bone cage 100 in the loaded position.

FIG. 9b illustrates an enlarged view of area 9b of FIG. 9a. To move bone cage placement device 100 from the unloaded position to the loaded position, selector knob 20 is rotated clockwise causing cam lift follower pins 13a, 13b, 13c (13b, 13c not visible) to move along cam-over surfaces 59a, 59b, 59c (59b, 59c not visible) in cam slots 43a, 43b, 43c (43b, 43c not visible) and come to rest in cam slots 44a, 44b, 44c (44b, 44c not visible). When selector knob 20 is in the final position, sliding implant engaging component 40 compresses positional spring 16 securing selector knob 20 in the loaded position. Cam-over surfaces 59a, 59b, 59c are higher than cam slots 44a, 44b, 44c and combined with constant spring pressure from positional spring 16, which is compressed, the selector knob 20 is prevented from slipping back into the unloaded position.

FIG. 10a illustrates an isometric view of an exemplary embodiment of selector tool 70 for bone cage placement device 100. Selector tool 70 is comprised of driver shaft 71, selector shaft 72, handle 74 having stop face 73, and cam lift driving feature 78.

After expandable bone cage 200 is loaded into bone cage placement device 100 and prior to the expandable bone cage 200 being implanted in the disc space between two vertebral bodies, selector tool 70 is inserted through instrument aperture 8 in proximal flat surface 2 of handle 10, through instrument aperture 31 of handle shaft 30, and through implant abutment shaft 50 (FIG. 1). When selector tool 70 is inserted into handle shaft 30 and expandable bone cage 200 is in the closed/first position, balls 65a, 65b (not visible) of ball spring plungers 11a, 11b mate into longitudinal grooves 77a of selector tool 70 (see FIGS. 10c and 11c).

Longitudinal grooves 77a, 77b, 77c (see FIG. 11c) have clearance space between balls 65a, 65b of ball spring plungers 11a, 11b and longitudinal grooves 77a, 77b, 77c so selector tool 70 slides easily into bone cage placement device 100 until balls 65a, 65b come in contact with peaks 76a (see FIGS. 10c and 11b). When balls 65a, 65b come in contact with peaks 76a, longitudinal force is applied to handle 74 of selector tool 70 overcoming the spring pressure in ball spring plungers 11a, 11b and causing balls 65a, 65b to retract to allow handle 74 to advance so that stop face 73 of selector tool 70 comes in contact with proximal flat surface 2 (see FIG. 1) of bone cage placement device 100.

When stop face 73 comes in contact with proximal flat surface 2, balls 65a, 65b advance into selector cavities 75a (first position, see FIGS. 10c and 11b). Selector cavities 75a are spherical and concave and retain balls 65a, 65b while expandable bone cage 200 is in the first position.

Figure 12B:
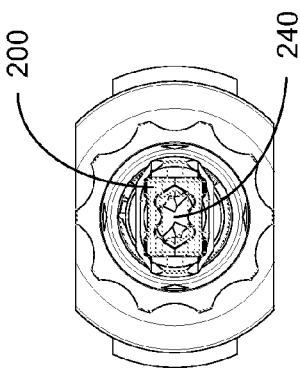
Figure 12A:
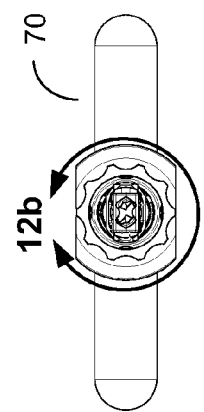
FIG. 12a illustrates a distal end view of an exemplary embodiment of a bone cage placement device with a selector tool in the first position and an expandable bone cage in the closed/first position.

When balls 65a, 65b are retained in selector cavities 75a, cam lift driving feature 78 is simultaneously mated into cam lift 240 of expandable bone cage 200, which is still in the first position (see FIGS. 12a and 12b). In FIGS. 12a and 12b, handle 74 is in its original position and expandable bone cage 200 and cam lift 240 are in the closed/first position.

Figure 13B:
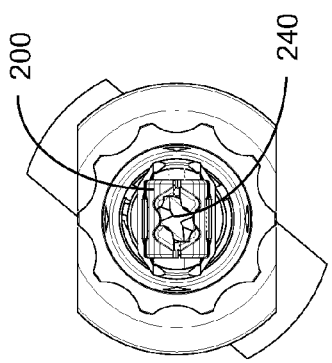
Figure 13A:
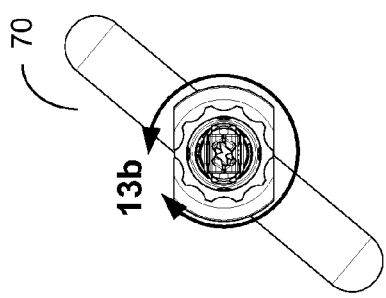
FIG. 13a illustrates a distal end view of an exemplary embodiment of a bone cage placement device with selector tool in the second position and an expandable bone cage expanded to the second position.

To expand expandable bone cage 200 to a second position, handle 74 of selector tool 70 is rotated to the second position (see FIGS. 13a and 13b). When handle 74 is rotated, balls 65a, 65b will retract and ride in concave radial selector groove 75b until balls 65a, 65b drop into selector cavities 75c (see FIG. 11b) and contact peaks 76b (see FIG. 11b). When balls 65a, 65b are in selector cavities 75c, expandable bone cage 200 and cam lift 240 are in the second expanded position as shown in FIGS. 13a and 13b.

To expand expandable bone cage 200 to the third position, handle 74 is rotated further. When handle 74 is rotated from the second position to the third position, balls 65a, 65b retract and ride in selector groove 75b until balls 65a, 65b drop into selector cavities 75d (see FIG. 11b) and contact peaks 76c (see FIGS. 10c and 11b).

FIG. 10b illustrates an enlarged view of area 10b of FIG. 10a showing driver shaft 71 and cam lift driving feature 78 of selector tool 70. Cam lift driving feature 78 is used to rotate cam lift 240 to expand expandable bone cage 200.

FIG. 10c illustrates an enlarged view of area 10c of FIG. 10a. Visible in FIG. 10c are selector groove 75b, selector cavities 75a, 75c, 75d, longitudinal grooves 77a, 77c, and peaks 76a, 76c.

FIG. 11a illustrates a side view of an exemplary embodiment of selector tool 70 for bone cage placement device 100.

FIG. 11b illustrates an enlarged view of area 11b of FIG. 11a showing selector shaft 72, six portions of radial selector groove 75b, selector cavities 75a, 75c, 75d, and peaks 76a, 76b, 76c.

FIG. 11c illustrates an enlarged view of area 11c of FIG. 11a showing selector shaft 72 and longitudinal grooves 77a, 77b, 77c.

FIG. 12a illustrates a distal end view of an exemplary embodiment of bone cage placement device 100 with selector tool 70 in the first position. When selector tool 70 is in the first position, expandable bone cage 200 is in the closed/first position.

FIG. 12b illustrates an enlarged view of area 12b of FIG. 12a showing selector tool 70 in the first position and expandable bone cage 200 in the closed/first position.

FIG. 13a illustrates a distal end view of an exemplary embodiment of bone cage placement device 100 with selector tool 70 in the second position. When selector tool 70 is rotated counterclockwise to the second position, expandable bone cage 200 is expanded to the second position.

FIG. 13b illustrates an enlarged view of area 13b of FIG. 13a showing selector tool 70 in the second position and expandable bone cage 200 expanded to the second position.

Figure 14B:
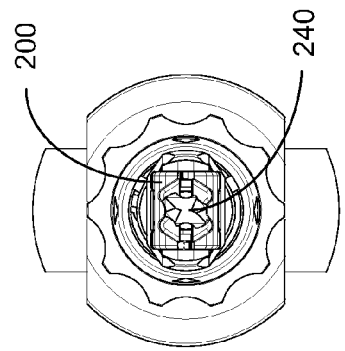
Figure 14A:
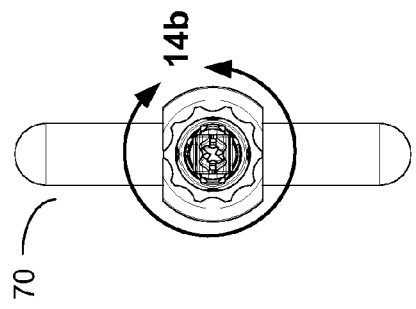
FIG. 14a illustrates a distal end view of an exemplary embodiment of a bone cage placement device and selector tool in the third position with an expandable bone cage expanded to a third position.

FIG. 14a illustrates a distal end view of an exemplary embodiment of bone cage placement device 100 and selector tool 70 in the third position. When selector tool 70 is rotated counterclockwise to the third and final position, expandable bone cage 200 is expanded to the third position.

FIG. 14b illustrates an enlarged view of area 14b of FIG. 14a showing selector tool 70 in the second position and expandable bone cage 200 expanded to the third position.

Figure 15A:
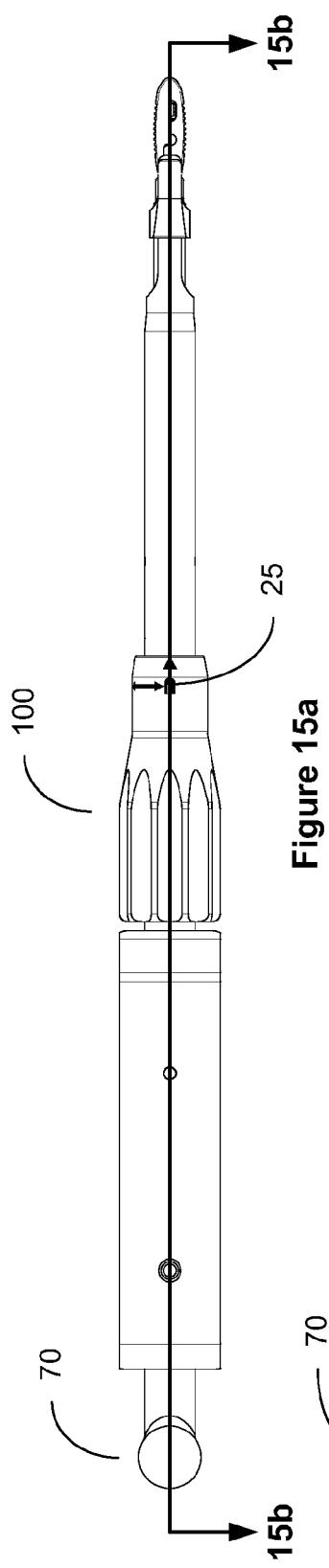
FIG. 15a illustrates a side view of an exemplary embodiment of a bone cage placement device with an expandable bone cage in the loaded position and a selector tool in the first position.

FIG. 15a illustrates a side view of an exemplary embodiment of bone cage placement device 100 with expandable bone cage 100 in the loaded position and selector tool 70 in the first position so that expandable bone cage 200 is closed. When bone cage placement device 100 is in the loaded position, U-shaped position marker 25 is visible on the right (and left) sides of bone cage placement device 100.

Figure 15B:
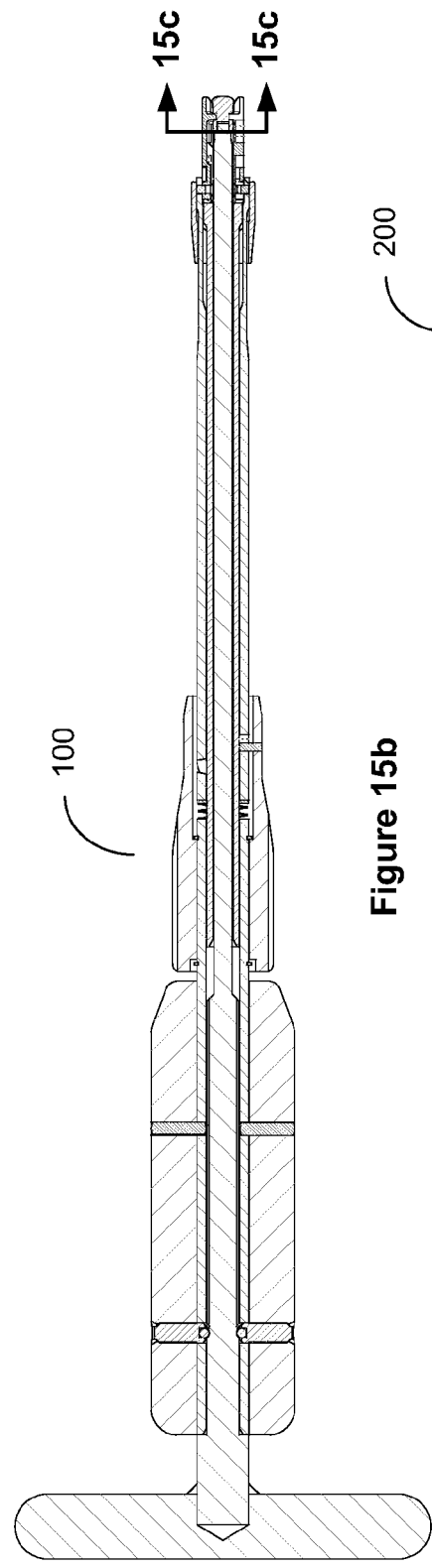

FIG. 15b illustrates a cross sectional view taken along line 15b of FIG. 15a showing selector tool 70 inside bone cage placement device 100.

Figure 15C:

FIG. 15c illustrates a cross sectional view taken along line 15c of FIG. 15a showing cam lift driving feature 78 inserted into cam lift 240 of expandable bone cage 200.

Figure 16:
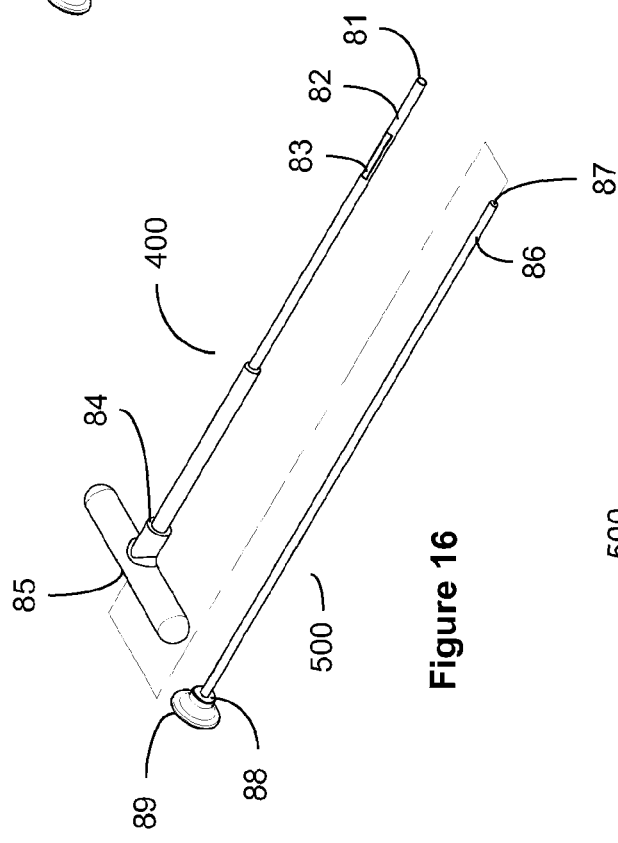
FIG. 16 illustrates an exploded isometric view of an exemplary embodiment of a graft placement tool and a graft placement plunger for a bone cage placement device.

FIG. 16 illustrates an exploded isometric view of an exemplary embodiment of graft placement tool 400 and graft placement plunger 500 for bone cage placement device 100. Graft placement tool 400 and graft placement plunger 500 are used to insert bone graft material 80 into expandable bone cage 200. After selector tool 70 is used to expand expandable bone cage 200, selector tool 70 is removed from bone cage placement device 100 and graft placement tool 400 is inserted into instrument aperture 8 in proximal flat surface 2 of handle 10 of bone cage placement device 100.

In the embodiment shown, graft placement tool 400 is comprised of plunger aperture 81, outer diameter 82, stop shoulder 84, and plunger surface 85. Outside diameter 82 further includes graft window 83 for inserting bone graft material 80.

In the embodiment shown, graft placement plunger 500 is comprised of outer diameter 86 having distal face 87, knob shoulder 88, and button 89. Distal face 87 of graft placement plunger 500 is inserted into plunger aperture 81 of graft placement tool 40 at plunger stop surface 85.

Figure 17:
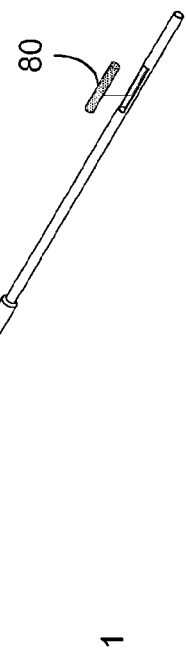
FIG. 17 illustrates an isometric view of an exemplary embodiment of a graft placement tool and a graft placement plunger in the loading position.

FIG. 17 illustrates an isometric view of an exemplary embodiment of graft placement tool 400 and graft placement plunger 500 in the loading position. Also visible is bone graft material 80 which is inserted into graft window 83 while plunger 500 is retracted.

In the embodiment shown, bone graft material 80 is cylindrically shaped; however, in an exemplary embodiment, bone graft material 80 is a paste that is loaded into graft window 83 using an applicator. In other embodiments, graft placement tool 400 does not include graft window 83, instead graft material 80 may be placed in the proximal end of plunger aperture 81 in a manner similar to loading a standard syringe.

Figure 18:
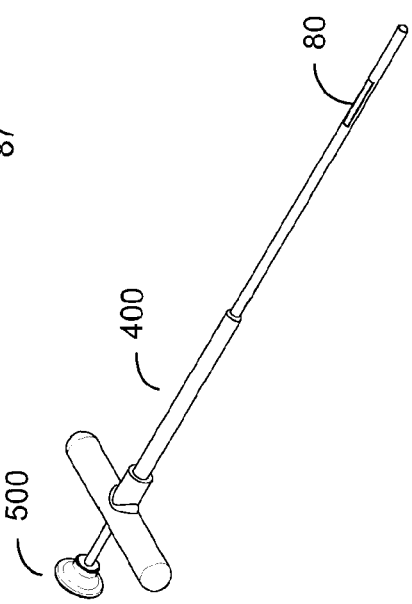
FIG. 18 illustrates an isometric view of an exemplary embodiment of a graft placement tool and a graft placement plunger loaded with bone graft material.

FIG. 18 illustrates an isometric view of an exemplary embodiment of graft placement tool 400 and graft placement plunger 500 loaded with bone graft material 80. In the embodiment shown, graft placement tool 400 and graft placement plunger 500 are ready for placement into bone cage placement device 100.

Figure 19A:
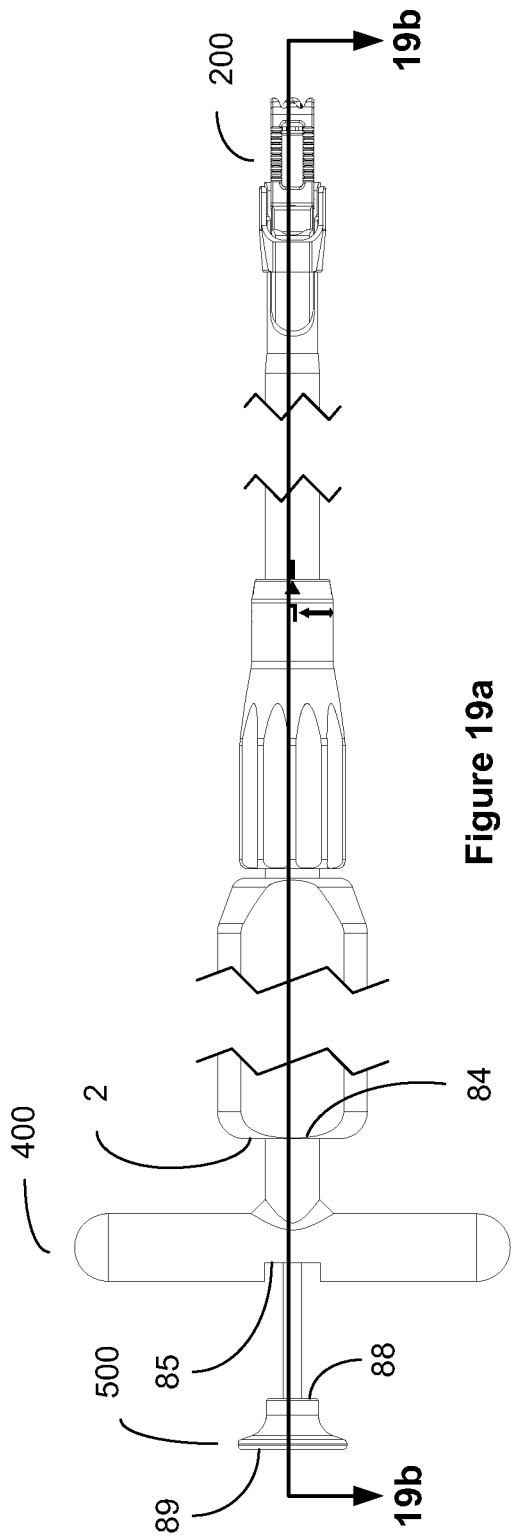
FIG. 19a illustrates a top view of an exemplary embodiment of a bone cage placement device with graft placement tool, graft placement plunger, and an expandable bone cage in the loaded position prior to placement of bone graft material.

FIG. 19a illustrates a top view of an exemplary embodiment of bone cage placement device 100 with graft placement tool 400, graft placement plunger 500, and expandable bone cage 200 in the loaded position prior to placement of bone graft material 80. Stop shoulder 84 of graft placement tool 400 is placed against proximal flat surface 2 of handle 10. When stop shoulder 84 is against proximal flat surface 2, the distal end of graft placement tool 400 is in position in expandable bone cage 200.

To insert bone graft material 80 into expandable bone cage 200, button 89 of plunger 500 is pushed until knob shoulder 88 is against plunger stop surface 85 of graft placement tool 400.

Figure 19B:
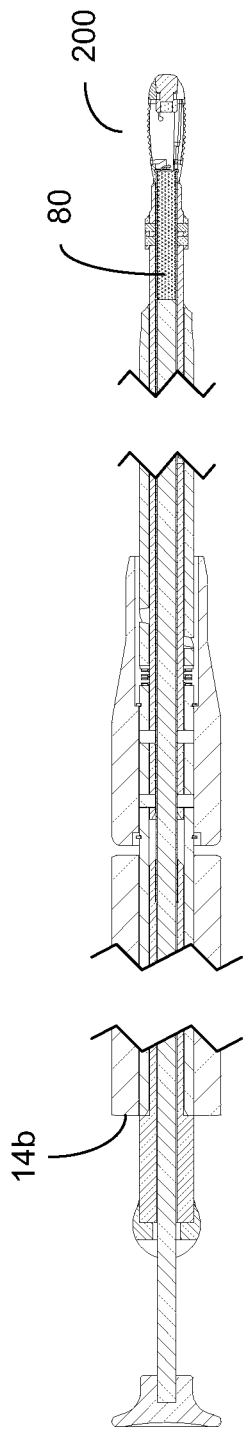

FIG. 19b illustrates a cross sectional view taken along line 19b of FIG. 19a showing bone graft material 80 in graft placement tool 400 prior to insertion into expandable bone cage 200.

Figure 20A:
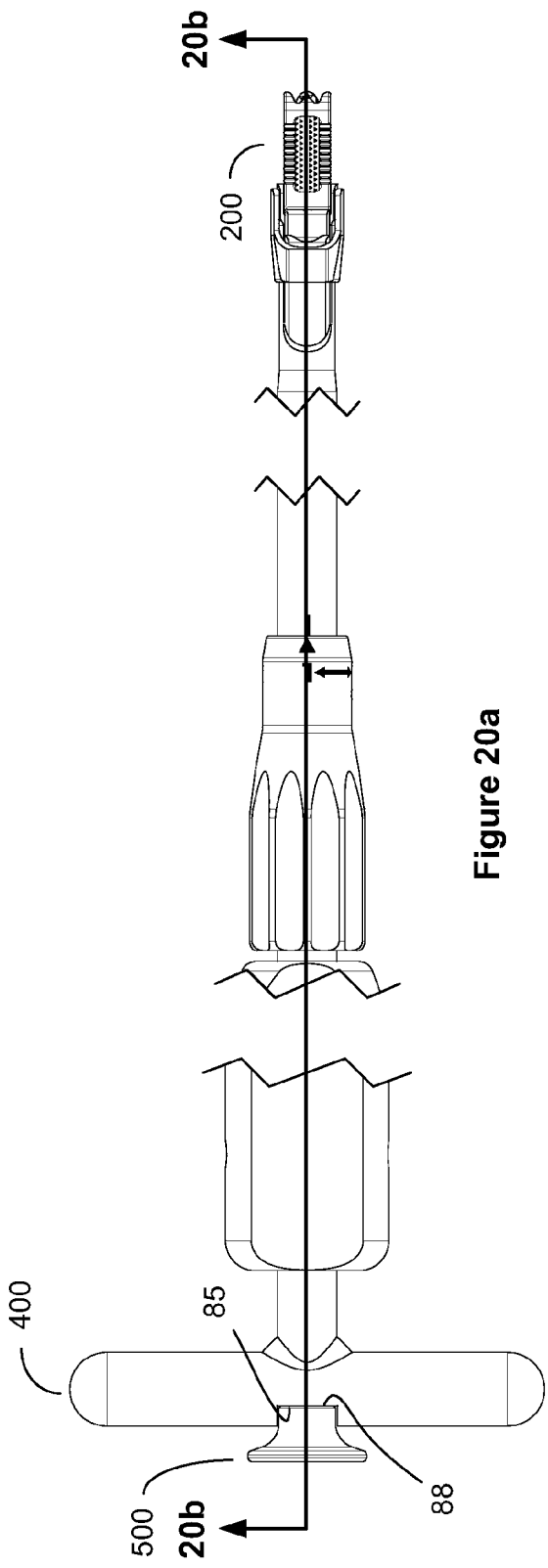
FIG. 20a illustrates a top view of an exemplary embodiment of a bone cage placement device with graft placement tool, graft placement plunger, and an expandable bone cage in the loaded position after placement of bone graft material.

FIG. 20a illustrates a top view of an exemplary embodiment of bone cage placement device 100 with graft placement tool 400, graft placement plunger 500, and expandable bone cage 200 in the loaded position after placement of bone graft material 80. In the embodiment shown, button 89 of plunger 500 has been pushed so that knob shoulder 88 rests against plunger stop surface 85 of graft placement tool 400, causing bone graft material 80 to be injected into expandable bone cage 200.

Figure 20B:
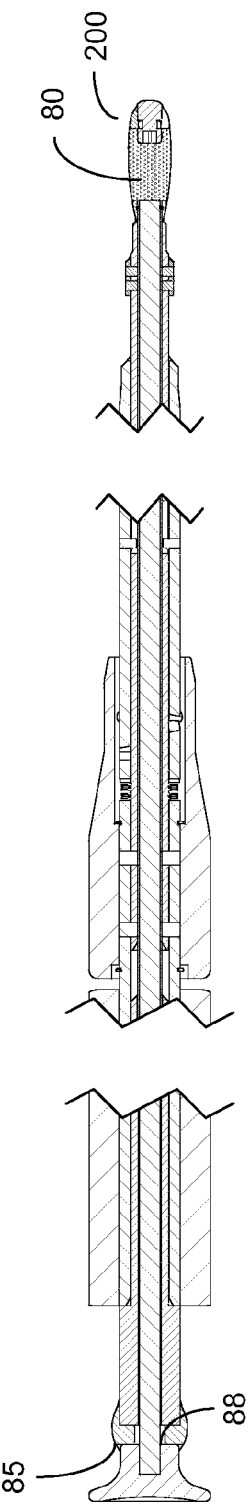

FIG. 20b illustrates a cross sectional view taken along line 20b of FIG. 20a showing bone graft material 80 injected into expandable bone cage 200.

FIG. 21 illustrates an isometric view of an exemplary embodiment of end plug installation tool 700 and end plug installer 800 for installing end plug 300 into expandable bone cage 200 after bone graft material 80 has been injected.

FIG. 22a illustrates an exploded isometric view of an exemplary embodiment of end plug installation tool 700, end plug installer 800, and end plug 300.

In the embodiment shown, end plug installation tool 700 is comprised of installer aperture 91, end plug tool outer diameter 92, end plug tool stop shoulder 93, and installer stop face 94.

In the embodiment shown, end plug installer 800 is comprised of installer outer diameter 95, installer plug face 96, installer shoulder 97, and installer button 98.

Also visible in FIG. 22a is an exemplary embodiment of end plug 300 for expandable bone cage 200. End plug 300 is inserted into the distal end of expandable bone cage 200 after bone graft material 80 has been injected. End plug 300 prevents bone graft material 80 from leaking out of expandable bone cage 200.

After bone graft material 80 is inserted into expandable bone cage 200, graft placement tool 400 and graft placement plunger 500 are removed from bone cage placement device 100. End plug installation tool 700 is then inserted into instrument aperture 8 in proximal flat surface 2 of handle 10 of bone cage placement device 100.

End plug 300 is placed into installer plug face 96 and pushed into position for installation into expandable bone cage 200 by applying pressure to installer button 98. After end plug 300 has been installed into installer plug face 96, end plug installer 800 is inserted into installer aperture 91 of end plug installation tool 700 at installer stop face 94 (see FIG. 23a).

Figure 23A:
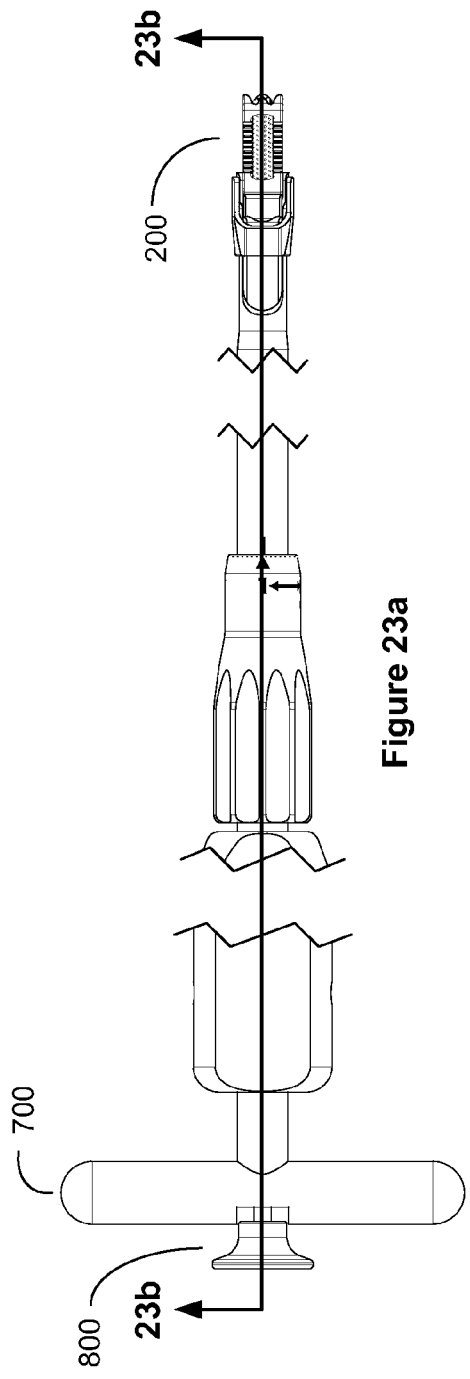
FIG. 23a illustrates a top view of a bone cage placement device with an expandable bone cage, an end plug installation tool, an end plug installer, and an end plug in the pre-loaded position.
Figure 23B:
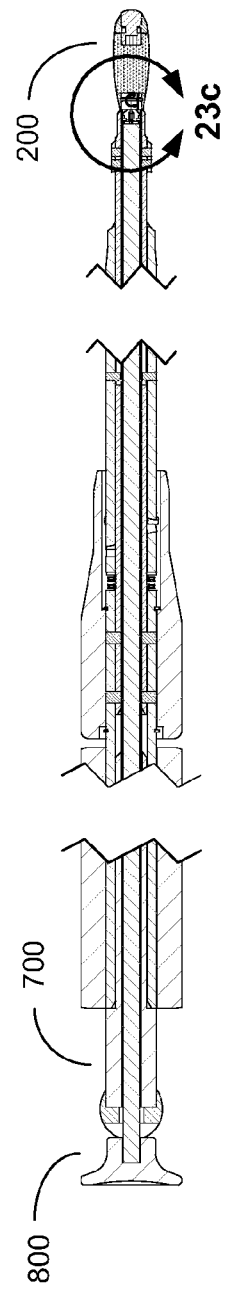

When end plug installer 800 is in the pre-loaded position, installer shoulder 97 is even with the end of end plug installation tool 700 (see FIGS. 23a and 23b). To install end plug 300 into expandable bone cage 200, installer button 98 is pushed into installer stop face 94 (see FIGS. 24a and 24b).

FIG. 22b illustrates an enlarged view of area 22b of FIG. 22a showing installer plug face 96 and end plug 300.

FIG. 23a illustrates a top view of bone cage placement device 100 with expandable bone cage 200, end plug installation tool 700, end plug installer 800, and end plug 300. In the embodiment shown, end plug installer 800 and end plug 300 are in the pre-loaded position.

FIG. 23b illustrates a cross sectional view taken along line 23b of FIG. 23a showing end plug installer 800 and end plug 300 in the pre-loaded position.

Figure 23C:
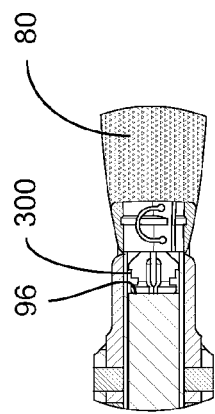
FIG. 23c illustrates an enlarged view of area 23c of FIG. 23b.

FIG. 23c illustrates an enlarged view of area 23c of FIG. 23b showing end plug installer 800 and end plug 300 in the pre-loaded position.

Figure 24A:
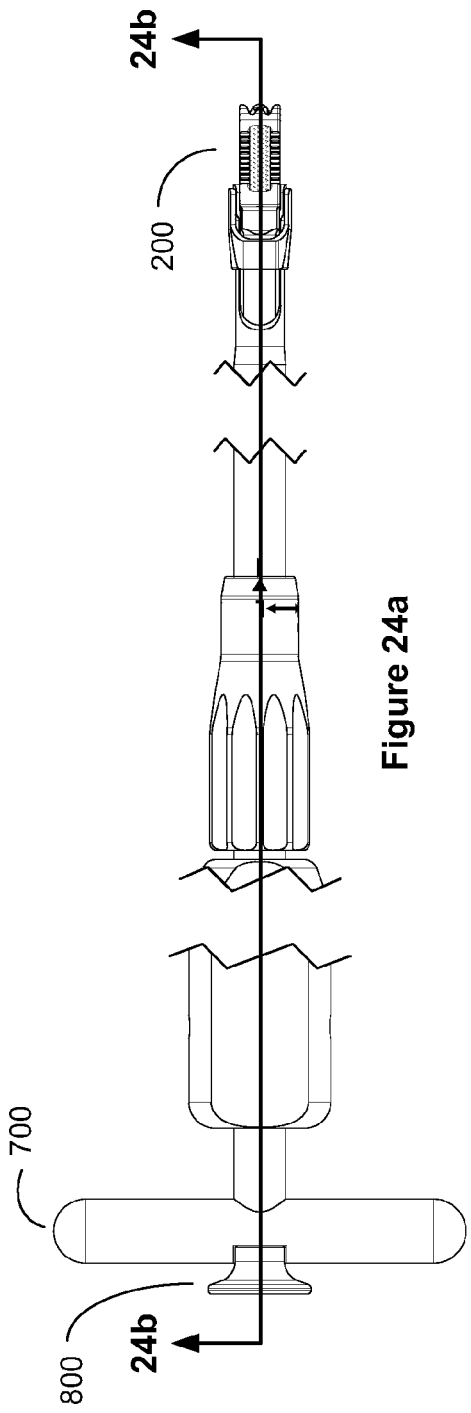
FIG. 24a illustrates a top view of an exemplary embodiment of a bone cage placement device with an expandable bone cage, an end plug installation tool, and an end plug installer in the final position showing an end plug inserted into the expandable bone cage.

FIG. 24a illustrates a top view of an exemplary embodiment of bone cage placement device 100 with expandable bone cage 200, end plug installation tool 700, and end plug installer 800 in the final position showing the end plug inserted into expandable bone cage 200.

Figure 24B:
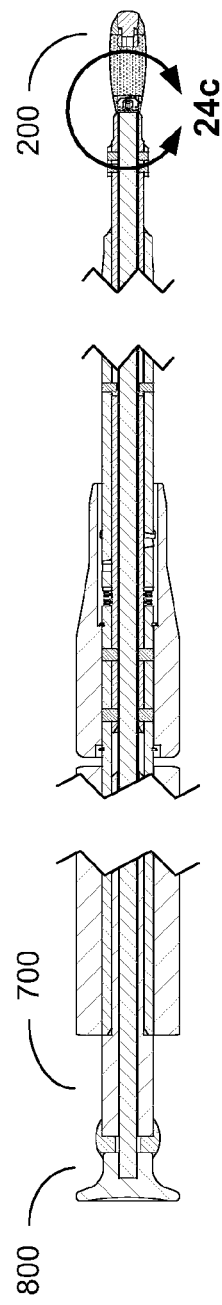

FIG. 24b illustrates a cross sectional view taken along line 24b of FIG. 24a showing end plug installer 800 in the final position and end plug 300 inserted in expandable bone cage 200.

Figure 24C:
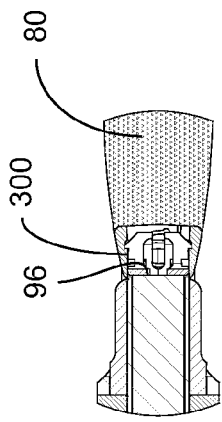
FIG. 24c illustrates an enlarged view of area 24c of FIG. 24b.

FIG. 24c illustrates an enlarged view of area 24c of FIG. 24b showing end plug installer 800 in the final position and end plug 300 inserted in expandable bone cage 200.

Once end plug 300 has been inserted in expandable bone cage 200, end plug installation tool 700, and end plug installer 800 may be removed. To remove bone cage placement device 100, selector knob 20 is turned counter-clockwise to the unloaded position, which retracts pins 49a, 49b from expandable bone cage 200. Bone cage placement device 100 may then be removed from the patient's body.

What is claimed is:

1. A bone cage placement apparatus for inserting an expandable bone cage for controlled expansion comprised of:
    an implant abutment shaft;
    a handle shaft, said handle shaft encircles a first end of said implant abutment shaft;
    a handle having a proximal flat surface with an instrument aperture, said handle encircles a first end of said handle shaft;
    a sliding implant engaging component, said sliding implant engaging component encircles a middle portion of said implant abutment shaft;
    a selector knob, said selector knob is adjacent to said handle and encircles a second end of said handle shaft and a first end of said sliding implant engaging component; and
    a reduction yoke, said reduction yoke encircles a second end of said implant abutment shaft.

2. The apparatus of claim 1 wherein said handle shaft is secured to said implant abutment shaft by a plurality of dowel pins inserted through apertures in said handle shaft and into apertures in said implant abutment shaft.

3. The apparatus of claim 1 wherein said handle is secured to said handle shaft by a plurality of dowel pins and ball spring plungers inserted through apertures in said handle and into apertures in said handle shaft.

4. The apparatus of claim 1 wherein said sliding implant engaging component is secured to said implant abutment shaft component by a plurality of alignment pins inserted through apertures in said sliding implant engaging component and into alignment slots in said implant abutment shaft.

5. The apparatus of claim 1 wherein said selector knob is secured to said sliding implant engaging component by a plurality of cam follower pins inserted through apertures in said selector knob and into clam slots in said sliding implant engaging component.

6. The apparatus of claim 1 wherein said reduction yoke is secured to said implant abutment shaft by a plurality of dowel pins inserted through apertures in said reduction yoke and into apertures in said implant abutment shaft.

7. The apparatus of claim 1 wherein said selector knob is rotated to load and unload said expandable bone cage.

8. The apparatus of claim 7 which further includes a plurality of position marks which designate the position of said expandable bone cage in said bone cage placement apparatus.

9. The apparatus of claim 1 which further includes a selector tool for expanding said expandable bone cage comprised of:

a selector tool handle;
a selector shaft;
a driver shaft; and
a cam lift driving feature.

10. The apparatus of claim 9 wherein said selector tool is inserted into said instrument aperture in said proximal flat surface of said handle and passes through said handle shaft and said implant abutment shaft of said bone cage placement apparatus.

11. The apparatus of claim 9 wherein said selector tool handle further includes a stop face which contacts said proximal flat surface of said handle.

12. The apparatus of claim 9 wherein said selector shaft further includes a selector groove, a plurality of selector cavities, a plurality of longitudinal grooves, and a plurality of peaks between said plurality of selector cavities and said plurality of longitudinal grooves.

13. The apparatus of claim 9 wherein said cam lift driving feature is inserted into said expandable bone cage and said selector tool handle is rotated to expand said expandable bone cage.

14. The apparatus of claim 1 which further includes a graft placement tool for inserting bone graft material into said expandable bone cage comprised of:
an outer diameter;
an aperture for inserting a graft placement plunger; and
a handle having a plunger surface and a stop shoulder.

15. The apparatus of claim 14 which further includes a graft window for inserting bone graft material.

16. The apparatus of claim 14 which further includes a graft placement plunger for inserting bone graft material into said expandable bone cage comprised of:
an outer diameter;
a distal face; and
a button having a knob shoulder.

17. The apparatus of claim 16 wherein said graft placement plunger is inserted into said aperture of said graft placement tool and said graft placement tool is inserted into said instrument aperture in said handle of said bone cage placement apparatus after said expandable bone cage has been expanded.

18. The apparatus of claim 1 which further includes an end plug installation tool for inserting an end plug into said expandable bone cage comprised of:
an outer diameter;
an aperture for inserting an end plug installer;
an installer aperture for inserting an end plug; and
a handle having a stop face and a stop shoulder.

19. The apparatus of claim 18 which further includes an end plug installer for inserting an end plug into said expandable bone cage comprised of:
an outer diameter;
a plug face; and
a button having a stop shoulder.

20. The apparatus of claim 19 wherein said end plug installer is inserted into said installer aperture of said end plug installation tool and said end plug installation tool is inserted into said instrument aperture in said handle of said bone cage placement apparatus after said bone graft material has been inserted into said expandable bone cage.

\* \* \* \* \*